United States Patent
Baba et al.

(10) Patent No.: US 9,071,170 B2
(45) Date of Patent: Jun. 30, 2015

(54) MOUNTING STRUCTURE FOR POLYMER ACTUATOR

(71) Applicant: TOYODA GOSEI CO., LTD., Kiyosu-shi, Aichi-ken (JP)

(72) Inventors: Kazumasa Baba, Kiyosu (JP); Hiromitsu Takeuchi, Kiyosu (JP)

(73) Assignee: TOYODA GOSEI CO., LTD., Aichi-pref. (JP)

( * ) Notice: Subject to any disclaimer, the term of this patent is extended or adjusted under 35 U.S.C. 154(b) by 152 days.

(21) Appl. No.: 13/753,580

(22) Filed: Jan. 30, 2013

(65) Prior Publication Data

US 2013/0207524 A1  Aug. 15, 2013

(30) Foreign Application Priority Data

Feb. 14, 2012  (JP) ................. 2012-029624

(51) Int. Cl.
| | |
|---|---|
| *H02N 2/00* | (2006.01) |
| *H01L 41/053* | (2006.01) |
| *H01L 41/083* | (2006.01) |
| *A61F 2/58* | (2006.01) |
| *A61F 2/68* | (2006.01) |
| *A61F 2/50* | (2006.01) |
| *A61F 2/70* | (2006.01) |

(52) U.S. Cl.
CPC ............... *H02N 2/00* (2013.01); *H01L 41/053* (2013.01); *H01L 41/0836* (2013.01); *A61F 2/588* (2013.01); *A61F 2/68* (2013.01); *A61F 2002/5066* (2013.01); *A61F 2002/6836* (2013.01); *A61F 2002/701* (2013.01)

(58) Field of Classification Search
CPC ....... H02N 2/00; H02N 2/0005; H02N 2/001; H02N 2/005; H02N 2/0055; H02N 2/02; H01L 41/053; H01L 41/0836
USPC .................................. 310/328, 800
See application file for complete search history.

(56) References Cited

U.S. PATENT DOCUMENTS 6,437,489 B1 *  8/2002  Shinke et al. ................. 310/369
7,514,850 B2 *  4/2009  Asai .............................. 310/328

(Continued)

FOREIGN PATENT DOCUMENTS

| JP | 2006-520180 A | 8/2006 |
|---|---|---|
| JP | 2008-277729 A | 11/2008 |

(Continued)

OTHER PUBLICATIONS

Office Action issued Jan. 6, 2015 in the corresponding JP application No. 2012-029624.

*Primary Examiner* — Derek Rosenau
(74) *Attorney, Agent, or Firm* — Posz Law Group, PLC

(57) ABSTRACT

A movable side mounting portion transmits extension and contraction of a polymer actuator to an electric prosthetic hand. The polymer actuator deforms elastically in accordance with voltage application and returns to its original shape in accordance with stoppage of voltage application. A rear end of the polymer actuator is fixed and a front end of the polymer actuator is movable. When one of a pair of electrodes of the polymer actuator is electrically connected to the fixed side mounting portion, the fixed end is fastened by a bolt to the fixed side mounting portion. Also, when the other electrode is electrically connected to the movable side mounting portion, the movable end is fastened by a bolt to the movable side mounting portion.

9 Claims, 5 Drawing Sheets

(56) References Cited

U.S. PATENT DOCUMENTS

2004/0217671 A1* 11/2004 Rosenthal et al. ............ 310/328
2008/0238258 A1 10/2008 Ishiguro et al.

FOREIGN PATENT DOCUMENTS

JP 2009-124875 A 6/2009
WO 2008/123090 A1 10/2008

* cited by examiner

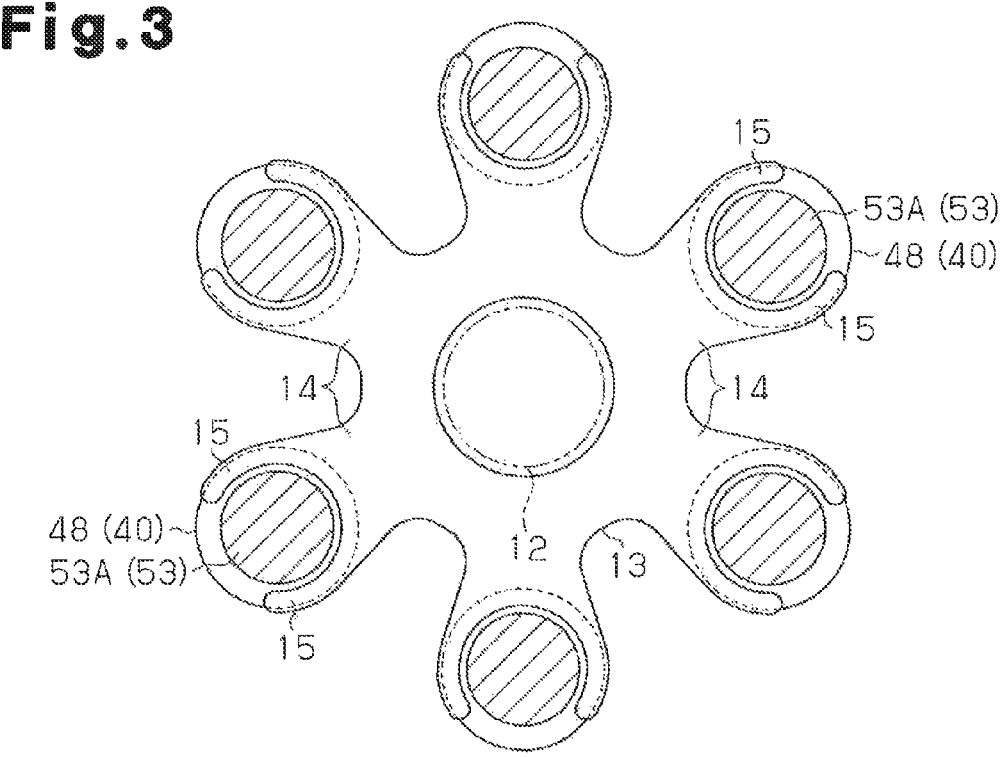
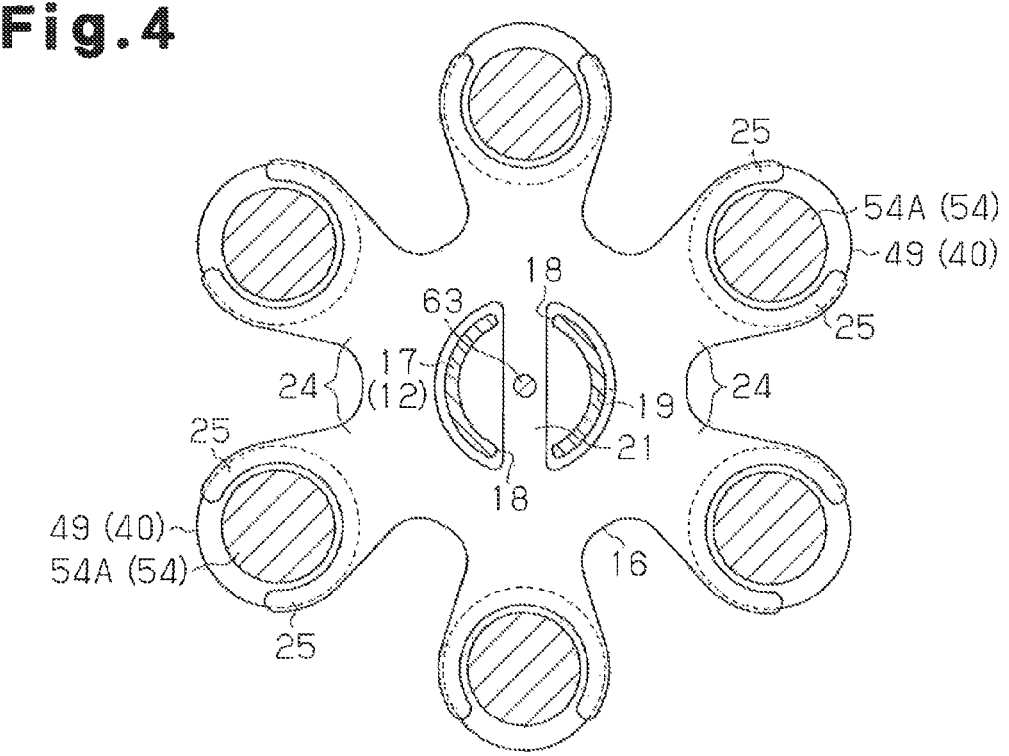

First finger portion side ← → Second finger portion side

Forward ↑ ↓ Rearward

MOUNTING STRUCTURE FOR POLYMER ACTUATOR

BACKGROUND OF THE INVENTION

The present invention relates to a mounting structure for a polymer actuator.

Japanese Laid-Open Patent Publication No. 2009-124875 discloses a polymer actuator that extends and contracts in an axial direction. The polymer actuator is made of a polymer material and is formed into an elongated shape. The polymer actuator deforms elastically in accordance with voltage application and returns to its original shape in accordance with stoppage of the voltage application. The polymer actuator includes an elastic dielectric layer and a pair of electrodes that sandwiches the dielectric layer from both sides. The dielectric layer is made of an insulating polymer material with elasticity, and each electrode is made of a conductive polymer material with elasticity. When a voltage is applied across the electrodes, the dielectric layer extends along its plane, and when the voltage application is stopped, the dielectric layer contracts and returns to its original shape. By using the polymer actuator as a drive source of an apparatus, the apparatus is made low in operation noise, and the weight of the apparatus is also lightened.

In an apparatus in which the above-described polymer actuator is incorporated, how electricity is supplied to the polymer actuator and how the extension and contraction of the polymer actuator are transmitted to the apparatus are important.

SUMMARY OF THE INVENTION

An objective of the present invention is to provide a mounting structure for a polymer actuator that is capable of supplying electricity to a polymer actuator and transmitting extension and contraction of the polymer actuator to an apparatus.

To achieve the foregoing objective and in accordance with one aspect of the present invention, a structure for mounting a polymer actuator onto an apparatus that includes the polymer actuator as a drive source is provided. The polymer actuator is made of a polymer material and is formed into an elongated shape. The polymer actuator deforms elastically in accordance with voltage application and returns to its original shape in accordance with stoppage of the voltage application, thereby extending and contracting in an axial direction of the polymer actuator. The apparatus operates using the extension and contraction of the polymer actuator. The mounting structure includes a fired side mounting portion, which is made of a conductive material, connected to a power supply, and arranged immovably, a movable side mounting portion, which is made of a conductive material, connected to the power supply, arranged to be reciprocal, and transmits extension and contraction of the polymer actuator to the apparatus, a fixed end, which is one of two ends of the polymer actuator, a movable end, which is the other of the two ends of the polymer actuator, a first fastening member, which electrically connects one of a pair of electrodes of the polymer actuator to the fixed side mounting portion and fastens the fixed end to the fixed side mounting portion, and a second fastening member, which electrically connects the other of the pair of electrodes of the polymer actuator to the movable side mounting portion and fastens the movable end to the movable side mounting portion.

BRIEF DESCRIPTION OF THE DRAWINGS

FIG. 3 is a cross-sectional view taken along line 3-3 in FIG. 1;

FIG. 4 is a cross-sectional view taken along line 4-4 in FIG. 2;

DETAILED DESCRIPTION OF THE PREFERRED EMBODIMENTS

A mounting structure for a polymer actuator according one embodiment of the present invention will now be described with reference to FIG. 1 to FIG. 8. The mounting structure is applied to an electric prosthetic hand, which is an apparatus. For illustrative purposes, forward and rearward directions are defined as shown in FIG. 1.

Figure 1:
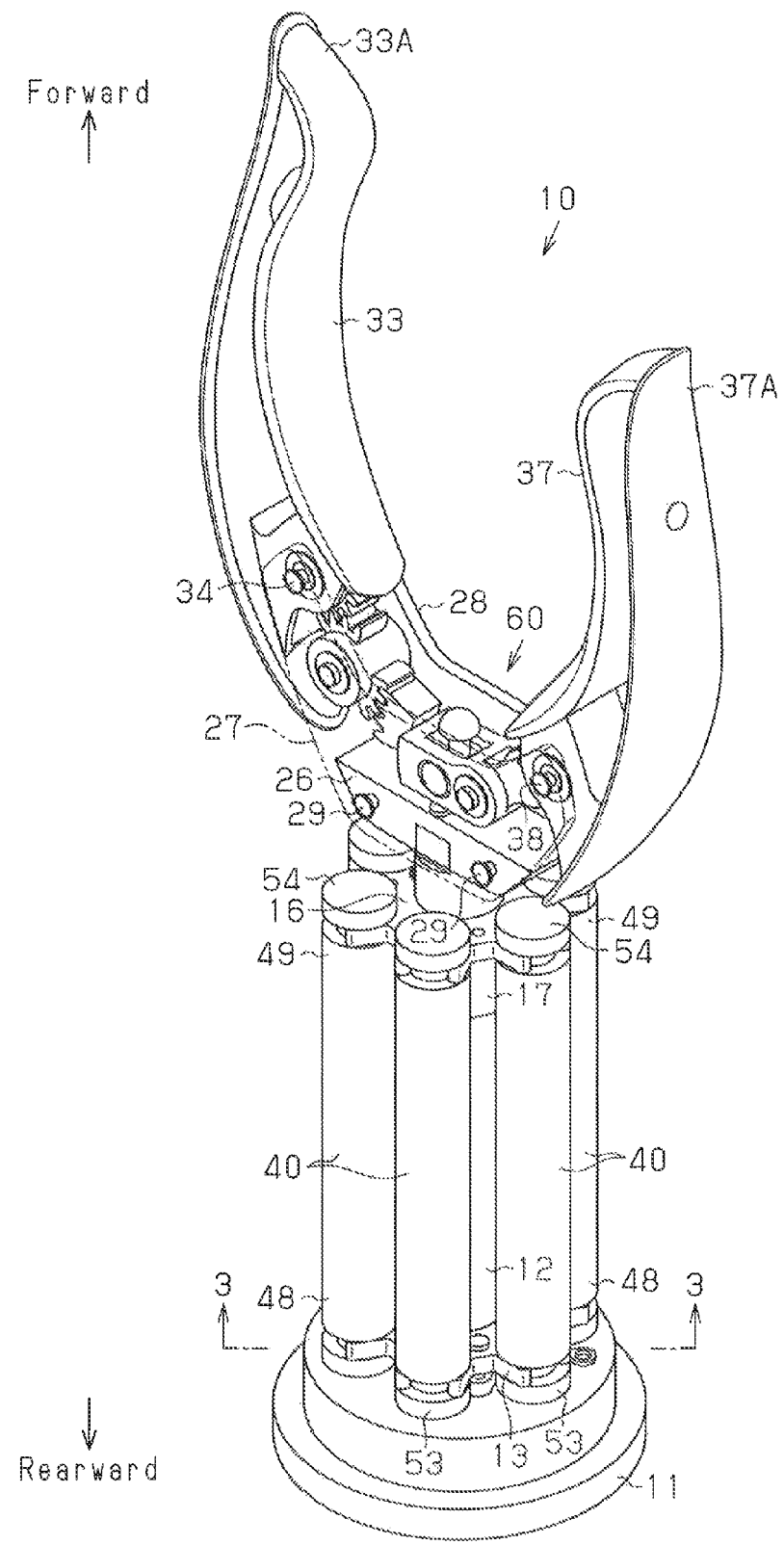
FIG. 1 is a perspective view of an electric prosthetic hand, to which a mounting structure for a polymer actuator according to the present invention is applied.
Figure 2:
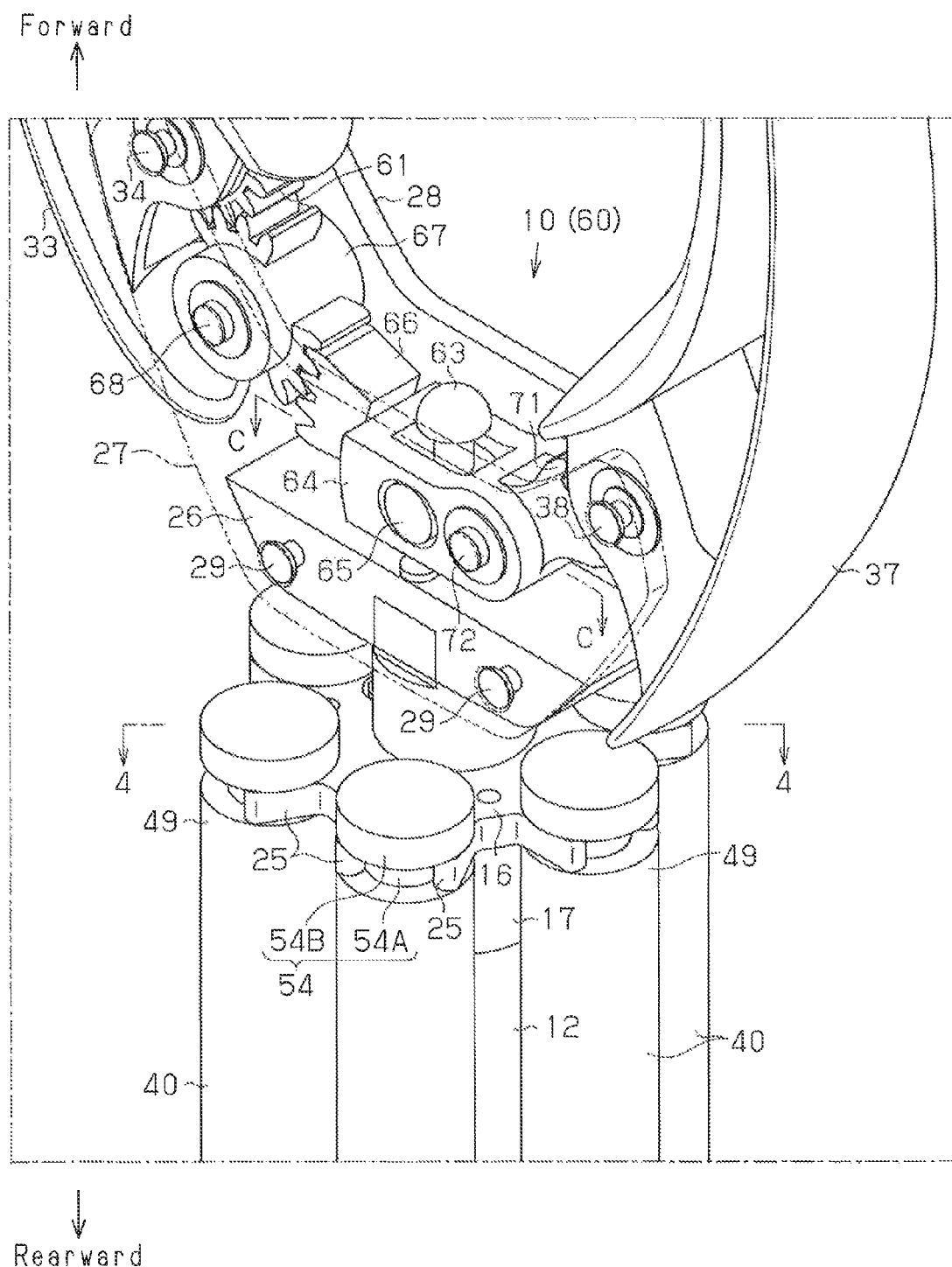
FIG. 2 is an enlarged partial perspective view showing a principal portion of FIG. 1.

As shown in FIGS. 1 and 2, the electric prosthetic hand includes a prosthetic hand main body 10, a plurality of finger portions, a plurality of polymer actuators 40, and a power transmitting portion 60. The prosthetic hand main body 10 is a framework portion of the electric prosthetic hand. The prosthetic hand main body 10 has a shape that is long in a front/rear direction. The prosthetic hand main body 10 has a base portion 11 at its rear portion. A support column 12 extends forward from a central portion of the base portion 11. A fixed side mounting portion 13 made of a conductive material is mounted to a rear end of the column 12. The fixed side mounting portion 13 is immovable in the front/rear direction and a circumferential direction with respect to the support column 12. The rear end of each polymer actuator 40 is mounted to the fixed side mounting portion 13. The single fixed side mounting portion 13 corresponds to the polymer actuators 40.

As shown in FIG. 3, the fixed side mounting portion 13 has a plurality of bulging portions 14, which bulge outward in radial directions of the support column 12. The bulging portions 14 are arranged at equiangular intervals around the support column 12. The number of the bulging portions 14 is the same as the number of the polymer actuators 40. The respective bulging portions 14 are mutually separated in the circumferential direction of the support column 12. Each bulging portion 14 includes a pair of clamping portions 15, which extends outward in radial directions of the support column 12.

As shown in FIGS. 1 and 2, a movable side mounting portion 16 made of a conductive material is mounted to a front portion of the support column 12. With respect to the support column 12, the movable side mounting portion 16 is immovable in the circumferential direction but is reciprocally movable in the front/rear direction. Front ends of the respective polymer actuators 40 are mounted to the movable side mounting portion 16. The single movable side mounting portion 16 corresponds to the polymer actuators 40.

A substantially cylindrical guide portion 17 is formed at least at a front portion of the support column 12. As shown in FIG. 4, the guide portion 17 has a groove 18 extending in the front/rear direction on each side of the center of the guide portion 17. An insertion hole 19, through which the guide portion 17 is inserted, is formed in a central portion of the movable side mounting portion 16. In the insertion hole 19 is provided a connecting portion 21, which passes through the center of the insertion hole 19 and connects two opposing locations on an inner wall surface of the insertion hole 19. The connecting portion 21 extends between the grooves 18. The grooves 18 allow reciprocal motion of the movable side mounting portion 16 in the front/rear direction while restricting rotation of the movable side mounting portion 16 around the guide portion 17.

The movable site mounting portion 16 has a plurality of bulging portions 24, which bulge outward in radial, directions of the insertion hole 19. The bulging portions 24 are arranged at equiangular intervals around the insertion hole 19. The number of the bulging portions 24 is the same as the number of the polymer actuators 40. The respective bulging portions 24 are mutually separated in the circumferential direction of the insertion hole 19. Each bulging portion 24 includes a pair of clamping portions 25, which extends outward in radial, directions of the insertion hole 19. The bulging portions 14 and the clamping portions 15 of the fixed side mounting portion 13 face the bulging portions 24 and the clamping portions 25 of the movable side mounting portion 16 in the front/rear direction.

Figures 6A, 6B:
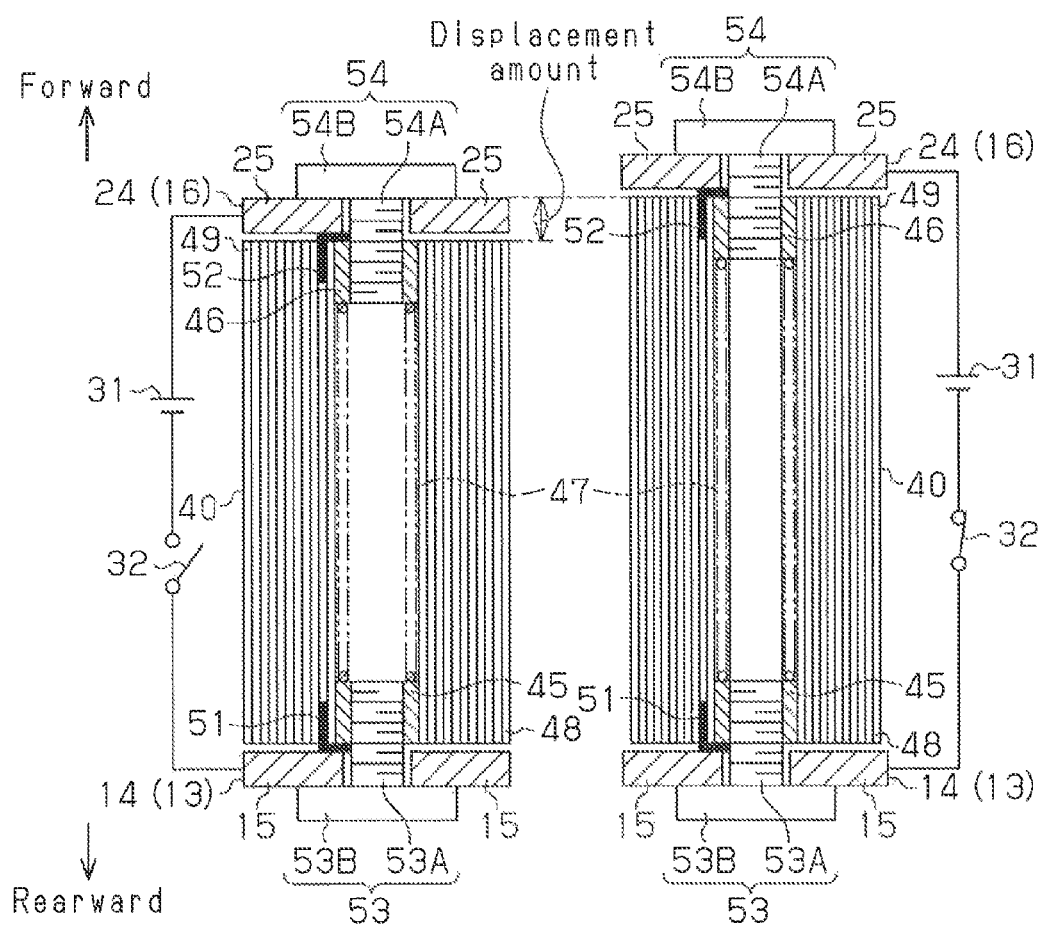
FIG. 6A is a cross-sectional view of the polymer actuator, which has contracted in accordance with stoppage of voltage application.
FIG. 6B is a cross-sectional view of the polymer actuator, which has extended in accordance with voltage application.

As shown in FIGS. 1 and 2, a joint portion 26 is fixed to the support column 12 at a front side relative to the movable side mounting portion 16. A pair of opposing wall portions 27 and 28, each having a plate-like shape, is located on respective sides of the joint portion 26. The opposing wall portions 27 and 28 are fixed to the side surfaces of the joint portion 26 by fastening members 29 such as screws. The opposing wall portion 27 is a portion corresponding to the back of a hand of a person and the opposing wall portion 28 is a portion corresponding to the palm of the hand. The opposing wall portion 27 is indicated by alternate long and two short dashed lines in FIGS. 1 and 2. As shown in FIG. 6A, one of the fixed side mounting portion 13 and the movable side mounting portion 16 is connected to a positive electrode of a power supply 31 and the other is connected to a negative electrode of the power supply 31 via a switch 32.

As shown in FIGS. 1 and 2, the finger portions include a first finger portion 33 and a second finger portion 37. The first finger portion 33 corresponds to an index finger, middle finger, or the like, of a hand of a person. A rear end of the first finger portion 33 is located, between first ends of the opposing wall portions 27 and 28 and is rotationally supported by a support shaft 34 installed between the opposing wall portions 27 and 28. The second finger portion 37 corresponds to a thumb of a hand of a person. A rear end of the second finger portion 37 is located between second ends of the opposing wall portions 27 and 28 and is rotationally supported by a support shaft 38 installed between the opposing wall portions 27 and 28.

Each polymer actuator 40 is made of a polymer material, deforms elastically in accordance with voltage application, and returns to its original shape in accordance with stoppage of the voltage application. The polymer actuator 40 thus extends and contracts in a manner similar to a muscle of a hand of a person. As the polymer actuator 40, a dielectric type polymer actuator, which is excellent in displacement, generated force, and the like, is adopted.

Figure 5:
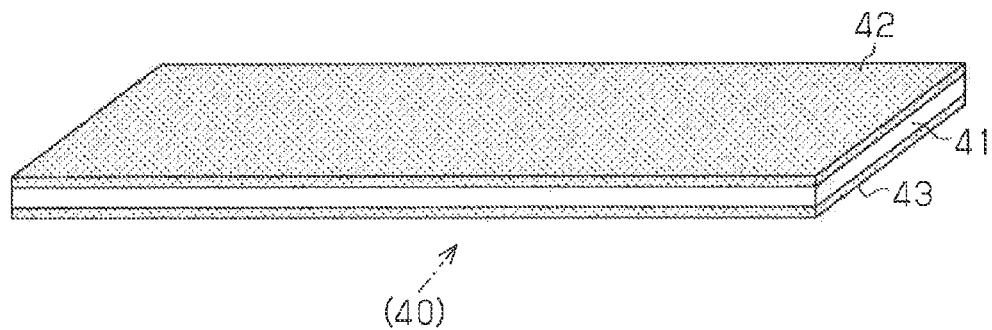
FIG. 5 is a perspective view of the polymer actuator in a developed form.

As shown in FIG. 5, the polymer actuator 40 includes a dielectric layer 41 made of an insulating polymer material with elasticity, and a pair of electrodes 42 and 43 made of a conductive polymer material with elasticity. The electrodes 42 and 43 sandwich the dielectric layer 41 in its thickness direction. The dielectric layer 41 is formed of a polymer compound with moving cross-link points, for example, a polymer gel, such as polyrotaxane. Both electrodes 42 and 43 are formed of a general-purpose rubber or the like.

The polymer actuator 40 causes the dielectric layer 41 to extend in its planar direction in accordance with voltage application across the electrodes 42 and 43. The polymer actuator 40 causes the dielectric layer 41 to contract and return to its original she in accordance with stoppage of the voltage application. As shown in FIGS. 6A and 63, a principal portion of the polymer actuator 40 is formed into a cylindrical shape with openings at both ends by spirally winding the dielectric layer 41 and the electrodes 42 and 43. Making the polymer actuator 40 compact improves the mountability in the electric prosthetic hand.

As shown in FIG. 6B, the polymer actuator 40 extends in the planar direction of dielectric layer 41, that is, the longitudinal direction of the polymer actuator 40 due to the voltage application across the electrodes 42 and 43. As shown in FIG. 6A, the polymer actuator 40 contracts in the longitudinal direction of the polymer actuator 40 and returns to its original shape due to the stoppage of the voltage application. Although a displacement amount of the actuator 40 during extension and contraction is small compared to a displacement amount of the finger portions 33 and 37 during opening and closing, the extension and contraction of the polymer actuator 40 is shown in exaggerated manner in FIGS. 6A and 6B.

Cylindrical internal thread members 45 and 46 are inserted and fixed at the respective open ends of each polymer actuator 40. Internal threads are formed on inner wall surfaces of the internal thread members 45 and 46. A coil spring 47 is compressed and located between the internal thread members 45 and 46. The coil spring 47 urges both internal thread members 45 and 46 in mutually separating directions. The urging force of the coil spring 47 is transmitted via the internal thread members 45 and 46 to the polymer actuator 40 and urges the polymer actuator 40 to extend it in its axial direction. This is done to suppress the dielectric layer 41 from extending in a spiral direction when it is to be extended in the planar direction and to increase a displacement amount of the polymer actuator 40 in the axial direction as much as possible.

As shown in FIGS. 1 and 2, the polymer actuators 40 are arranged with the extension/contraction direction of each polymer actuator 40 being matched with the front/rear direction of the prosthetic hand main body 10. As shown in FIGS. 6A and 6B, the rear end of the polymer actuator 40 is the fixed end 48, and the front end of the polymer actuator 40 is the movable end 49. Electrode lead portions 51 and 52 are provided at respective end surfaces of the fixed end 48 and the movable end 49. The electrode lead portion 51 is electrically connected to one of the two electrodes 42 and 43, and the electrode lead portion 52 is electrically connected to the other of the two electrodes 42 and 43.

Each polymer actuator 40 is located between a pair of clamping portions 15 provided at the corresponding bulging portion 14 of the fixed side mounting portion 13 and a pair of clamping portions 25 provided at the corresponding bulging portion 24 of the movable side mounting portion 16. The fixed end 48 of each polymer actuator 40 is fastened to the corresponding bulging portion 14 of the fixed side mounting portion 13 by a bolt 53 as a first fastening member. The bolt 53 is made up of a shaft portion 53A having an external thread and a head portion 53B provided at the rear end of the shaft portion 53A. The shaft portion 53A is passed between the clamping portions 15 from the rear of the fixed side mounting portion 13 and screwed into the internal thread member 45 near the fixed end 48. When the bolt 53 is screwed, the electrode lead portion 51 is pressingly contacted with the fixed side mounting portion 13. Also, one of the electrodes 42 and 43 is electrically connected to the fixed side mounting portion 13 via the electrode lead portion 51. Also, the fixed end 48 of the polymer actuator 40 is fastened to the fixed side mounting portion 13.

Also, the movable end 49 of each polymer actuator 40 is fastened to the corresponding bulging portion 24 of the movable side mounting portion 16 by a bolt 54 as a second fastening member. The bolt 54 is made up of a shaft portion 54A having an external thread and a head portion 54B provided at the front end of the shaft portion 54A. The shaft portion 54A is passed between the clamping portions 25 from the front of the movable side mounting portion 16 and screwed into the internal thread member 46 near the movable end 49. When the bolt 54 is screwed, the electrode lead portion 52 is pressingly contacted with the movable side mounting portion 16. Also, the other of the electrodes 42 and 43 is electrically connected to the movable side mounting portion 16 via the electrode lead portion 51. Also, the movable end 49 of the polymer actuator 40 is fastened to the movable side mounting portion 16.

As shown in FIGS. 1 and 2, the power transmitting portion 60 is provided between the movable side mounting portion 16 and the support shafts 34 and 38 of the respective finger portions 33 and 37. The power transmitting portion 60 converts a front/rear movement of the movable side mounting portion 16 associated with the extension and contraction of each polymer actuator 40 into a rotational motion. The power transmitting portion 60 then transmits the rotational motion, resulting from the conversion, to the respective finger portions 3 and 37, thereby rotating, that is, causing the finger portions 33 and 37 to open or close. A driven gear 61 is provided at the rear end of the first finger portion 33 near the support shaft 34. A driven gear is provided at the rear end of the second finger portion 37 near the support shaft 38.

Figure 7:
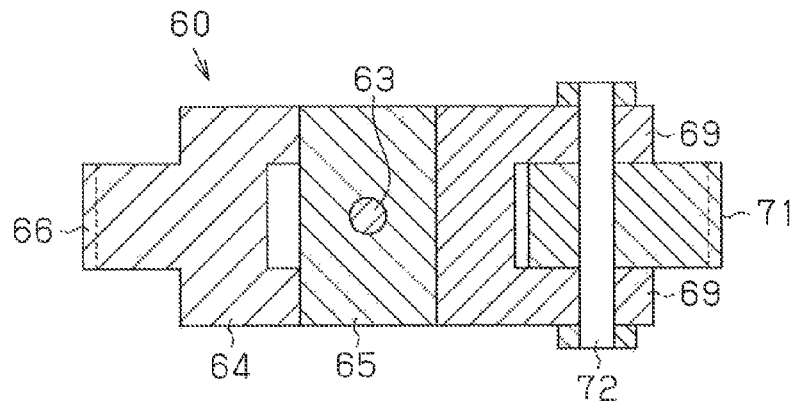
FIG. 7 is cross-sectional view taken along line 7-7 in FIG. 2.

Meanwhile, as shown in FIGS. 2 and 4, a drive pin 63 is fixed at a center of the movable side mounting portion 16 or the connecting portion 21. The drive pin 63 is located between the support shafts 34 and 38, extends forward from the movable side mounting portion 16, and is inserted through the joint portion 26. As shown in FIGS. 2 and 7, between the support shafts 34 and 38 and in front of the joint, portion 26, a transmission member 64 is arranged to surround the drive pin 63. The transmission member 64 is connected to the drive pin 63 by a connecting shaft 65. The axis of the connecting shaft 65 is orthogonal to the axis of the drive pin 63.

A drive gear 66 is mounted at an end of the transmission member 64 near the first finger portion 33. A transmission gear 67 is rotationally supported by a shaft 68 between the opposing wall portions 27 and 28 and between the drive gear 66 and the driven gear 61. The transmission gear 67 is meshed with both the drive gear 66 and the driven gear 61. On the other hand, a pair of support wall portions 69 is provided at a portion of the transmission member 64 near the second finger portion 37. A drive gear 71 is located between the support wall portions 69. The drive gear 71 is rotationally supported by the support wall portions 69 via a shaft 72. The drive gear 71 is meshed with the driven gear of the second finger portion 37.

The polymer actuators 40 are mounted as follows to the electric prosthetic hand described above. As shown at a left side of FIG. 8, the bolt 53 is screwed loosely to the internal thread member 45 fixed near the fixed end 48 of each polymer actuator 40. Also, the bolt 54 is screwed loosely in the internal thread member 46 fixed near the movable end 49 of each polymer actuator 40. The bolts 53 and 54 are screwed such that the interval between the head portion 53B and the head portion 54B is slightly greater than the length of each polymer actuator 40 when it is contracted, that is, slightly greater than the interval between the electrode lead portions 51 and 52.

Figure 8:
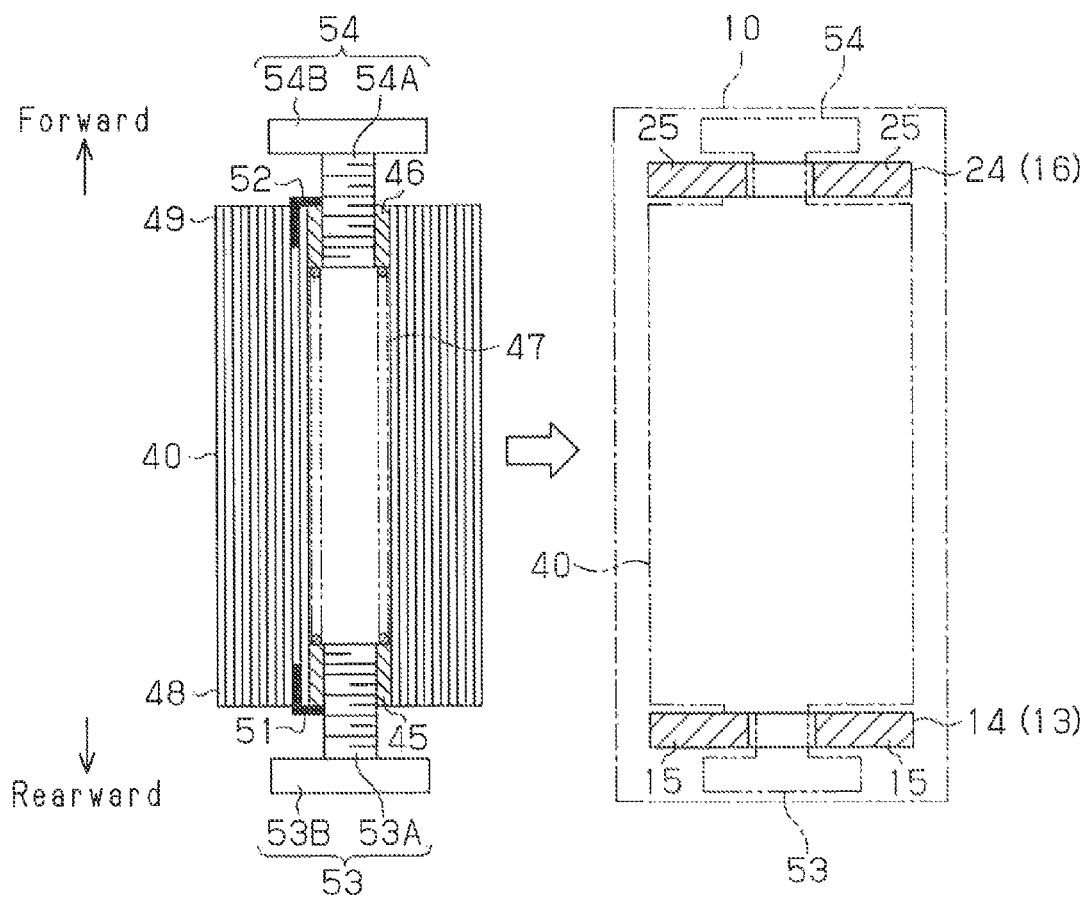
FIG. 8 is a cross-sectional view of the polymer actuator before being mounted to a fixed side mounting portion and a movable side mounting portion of a prosthetic hand main body.

Thereafter, as indicated by alternate long and two short dashed lines at a right side of FIG. 8, the polymer actuator 40 is located between the fixed side mounting portion 13 and the movable side mounting portion 16. At this point, the tips of the respective clamping portions 15 are separated from each other at each bulging portion 14 of the fixed side mounting portion 13. The shaft portion 53A of the bolt 53 can thus pass between the clamping portions 15. Similarly, at each bulging portion 24 of the movable side mounting portion 16, the tips of the respective clamping portions 25 are separated from each other. The shaft portion 54A of the bolt 54 can thus pass between the clamping portions 25.

The shaft portion 53A of the bolt 53, which has been screwed into the internal thread member 45, is inserted between the clamping portions 15 from outside the fixed side mounting portion 13. Also, the shaft portion 54A of the bolt 54, which has been screwed into the internal thread member 46, is inserted between the clamping portions 25 from outside the movable side mounting portion 16. When the bolt 53 is screwed further, the electrode lead portion 51 and the fixed side mounting portion 13 are sandwiched by the head portion 53B and the fixed end 48. The bolt 53 is screwed until the clearance between the fixed end 48 and the fixed side mounting portion 13 is eliminated or the clearance falls within an allowable range. The electrode lead portion 51 is consequently pressed by the fixed side mounting portion 13 as shown in FIG. 6A, and thus one of the two electrodes 42 and 43 is electrically connected to the fixed side mounting portion 13 via the electrode lead portion 51. The fixed end 48 is also fastened to the fixed side mounting portion 13.

Similarly, when the bolt 54 is screwed, the electrode lead portion 52 and the movable side mounting portion 16 are sandwiched by the head portion 54B and the movable end 49. The bolt 54 is screwed until the clearance between the movable end 49 and the movable side mounting portion 16 is eliminated or the clearance falls within an allowable range. The electrode lead portion 52 is consequently pressed by the movable side mounting portion 16 as shown in FIG. 6A, and thus the other of the two electrodes 42 and 43 is electrically connected to the movable side mounting portion 16 via the electrode lead portion 52. The movable end 49 is also fastened to the movable side mounting portion 16. The polymer actuators 40 are thus mounted one-by-one between the fixed side mounting portion 13 and the movable side mounting portion 16. The above series of processes is performed for all of the polymer actuators 40.

To remove the polymer actuators 40 from the electric prosthetic hand, processes that are reverse the above series or processes are performed. Specifically, when as shown in FIG. 6A, the bolt 53 is loosened, the head portion 53B separates rearward from the fixed end 48 so that the electrode lead portion 51 and the fixed end 48 are no longer pressed by the fixed side mounting portion 13. Similarly, when the bolt 54 is loosened, the head portion 54B separates forward from the movable end 49 so that the electrode lead portion 52 and the movable end 49 are no longer pressed by the movable side mounting portion 16. The shaft portion 53A of the bolt 53 is then extracted outward from between the clamping portions 15 of the fixed side mounting portion 13. Similarly, the shaft portion 54A of the bolt 54 is extracted outward from between the clamping portions 25 of the movable side mounting portion 16. The above series of processes is also performed for all of the polymer actuators 40.

Operation of the electric prosthetic hand of present embodiment will now be described.

FIGS. 1 and 2 shows the electric prosthetic hand when the switch 32 shown in FIG. 6 is opened. In this state, the voltage application across the electrodes 42 and 43 of each polymer actuator 40 is stopped. In the state shown in FIG. 6A, charges are released and discharged. Therefore, charges are not accumulated in either of the electrodes 42 and 43 of each polymer actuator 40. Each polymer actuator 40 is thus contracted.

The fixed ends 48 of the polymer actuators 40 are fixed to the common fixed side mounting portion 13. The positions in the front/rear direction of the fixed ends 48 thus do not change. On the other hand, the movable ends 49 of the polymer actuators 40, although being mounted to the common movable side mounting portion 16, are not fixed to the prosthetic hand main body 10. The movable end 49 of each polymer actuator 40 is located at the most rearward position of the movable range. Meanwhile, the movable side mounting portion 16, to which the movable end 49 is mounted, is also positioned at the most rearward position of the movable range. In this state, a fingertip 33A of the first finger portion 33 and a fingertip 37A of the second finger portion 37 are separated widely.

When from the above state, an object to be held is held by the electric prosthetic hand, the switch 32 shown in FIG. 6B is closed. In this process, a voltage is applied across the electrodes 42 and 43 of each polymer actuator 40. One of the electrodes 42 and 43 thereby becomes positively charged and the other becomes negatively charged. After the voltage application, although a current flows until predetermined amounts of charges become accumulated in the respective electrodes 42 and 43, when the predetermined amounts of charges are accumulated, hardly any current flows. That hardly any current flows means that, due to occurrence of discharge after the accumulation of the predetermined amounts of charges, a current does flow for compensation of charges that are decreased by the discharge.

When both electrodes 42 and 43 become charged as described above, an attractive Coulomb force is generated between the electrodes 42 and 43. In this process, the dielectric layer 41 is pressed in the thickness direction of the dielectric layer 41 by the electrodes 42 and 43 and extends in the planar direction of the dielectric layer 41. Also in this process, the electrodes 42 and 43 follow the dielectric layer 41 and extend because of being formed from conductive polymer materials with elasticity. Consequently, each polymer actuator 40 extends in the planar direction of the dielectric layer 41, that is, in the longitudinal direction of the polymer actuator 40. By extension of the polymer actuator 40, the movable end 49 moves forward and separates from the fixed end 48. Accordingly, the movable side mounting portion 16, to which the movable end 49 is mounted, also moves forward, in this process, the movable side mounting portion 16 moves forward while being restricted in movement in the circumferential direction by the guide portion 17.

As shown in FIG. 2, in accordance with the forward movement of the movable side mounting portion 15, the drive pin 63 also moves forward together with the movable side mounting portion 16. The transmission member 64 also moves forward because the movement of the drive pin 63 is transmitted via the connecting shaft 65 to the transmission member 64. The forward movement of the transmission member 64 is transmitted to the first finger portion 33 via the drive gear 66, the transmission gear 67, and the driven gear 61. The first finger portion 33 is thereby rotated clockwise in FIG. 1 with the support shaft 34 as a supporting point and the fingertip 33A of the first finger portion 33 approaches the fingertip 37A of the second finger portion 37. The forward movement of the transmission member 64 is also transmitted to the second finger portion 37 via the drive gear 71 and the driven gear. The second finger portion 37 is thereby rotated counterclockwise in FIG. 1 with the support shaft 38 as a supporting point and the fingertip 37A of the second finger portion 37 approaches the fingertip 33A of the first finger portion 33. Consequently, the object to be held can be held by the fingertips 37A and 33A.

When as shown in FIG. 6A, the switch 32 is opened again from the above described state, the voltage application across the electrodes 42 and 43 of each polymer actuator 40 is stopped. The charges accumulated in the electrodes 42 and 43 are thereby released and discharged. The amounts of charges charged in the electrodes 42 and 43 then decrease and the attractive Coulomb force decreases. The dielectric layer 41 thus contracts in the planar direction of the dielectric layer 41 due to its own elastic force. Consequently, as shown in FIG. 6A, each polymer actuator 40 contracts in the planar direction of the dielectric lever 41, that is, in the longitudinal direction of the polymer actuator 40. In this process, the electrodes 42 and 43 also follow the dielectric layer 41 and contract. By contraction of the polymer actuator 40, the movable end 49 moves rearward and approaches the fixed end 48. Accordingly, the movable side mounting portion 16, to which the movable end 49 is mounted, also moves rearward. In this process, the movable side mounting portion 16 moves rearward while being restricted in movement in the circumferential direction by the guide portion 17.

In accordance with the rearward movement of the movable side mounting portion 16, the drive pin 63 also moves rearward together with the movable side mounting portion 16. The transmission member 64 also moves rearward because the movement of the drive pin 63 is transmitted via the connecting shaft 65 to the transmission member 64. The rearward movement of the transmission member 64 is transmitted to the first finger portion 33 via the drive gear 66, the transmission gear 67, and the driven gear 61. The first finger portion 33 is thereby rotated counterclockwise in FIG. 1 with the support shaft 34 as the supporting point and the fingertip 33A of the first finger portion 33 moves away from the fingertip 37A of the second finger portion 37. The rearward movement of the transmission member 64 is also transmitted to the second finger portion 37 via the drive gear 71 and the driven gear. The second finger portion 37 is thereby rotated clockwise in FIG. 1 with the support shaft 38 as the supporting point and the fingertip 37A of the second finger portion 37 moves away from the fingertip 33A of the first finger portion 33.

The extension and contraction of the polymer actuators 40 is thus converted to a rotational motion by the power transmitting portion 60 and then transmitted to each of the first finger portion 33 and the second finger portion 37. When, in this process, the force generated during extension of each polymer actuator 40 is small, the force applied to the movable side mounting portion 16 will also be small. In regard to this point, with the present embodiment, the polymer actuators 40 are used and the polymer actuators 40 are mounted to the common movable side mounting portion 16 with the respective polymer actuators 40 being matched in extension and contraction direction. By this arrangement, a large force is applied to the movable side mounting portion 16 and thus the force by which an object to be held is held by the finger portions 33 and 37 is increased.

Also, the polymer actuators 40, each including the dielectric layer 41, which is made of the insulating polymer material, and the electrodes 42 and 43, which are made of the conductive polymer material, are used as the drive source that drives the first finger portion 33 and the second finger portion 37. This arrangement can be made lighter than a drive source made up of metal parts, such as an electric motor or electromagnetic actuator. The electric prosthetic hand can thus also be made light as a whole.

By the present embodiment, the following advantages are achieved.

(1) The fixed side mounting portion 13, which is made of the conductive material and connected to the power supply 31, is arranged immovably. Also, the movable side mounting portion 16, which is made of the conductive material and connected to the power supply 31, is arranged to be reciprocal. The movable side mounting portion 16 transmits the extension and contraction of the polymer actuators 40 to the power transmitting portion 60 of the electric prosthetic hand. The rear end of each polymer actuator 40 is the fixed end 48 and the front end of each polymer actuator 40 is the movable end 49. In the state where one of the two electrodes 42 and 43 is electrically connected to the fixed side mounting portion 13, the fixed end 48 is fastened to the fixed side mounting portion 13 by the first fastening member. In the state where the other of the two electrodes 42 and 43 is electrically connected to the movable side mounting portion 16, the movable end 49 is fastened to the movable side mounting portion 16 by the second fastening member. By this arrangement, electricity can be supplied to the polymer actuators 40 via the fixed side mounting portion 13 and the movable side mounting portion 16. Also, the power transmitting portion 60 can be put in operation and the finger portions 33 and 37 can be opened or closed by the movable side mounting portion 16, which moves in accordance with the extension or contraction of the polymer actuators 40. The mounting structure for the polymer actuators 40 by which electricity is supplied to the polymer actuators 40 and the extension and contraction of the polymer actuators 40 is transmitted to the electric prosthetic hand can thus be provided.

(2) Each polymer actuator 40 includes the dielectric layer 41, which is made of an insulating polymer material having elasticity, and the electrodes 42 and 43, which are made of a conductive polymer material having elasticity. The electrodes 42 and 43 sandwich the dielectric layer 41 from its thickness direction. With this arrangement, the polymer actuator 40 causes the dielectric layer 41 to extend in its planar direction in accordance with the voltage application across the electrodes 42 and 43. The polymer actuator 40 causes the dielectric layer 41 to contract and return to its original shape in accordance with the stoppage of the voltage application. Also, after the voltage application, although current flows until the predetermined amounts of charges become accumulated in the respective electrodes 42 and 43, when the predetermined amounts of charges are accumulated, hardly any current flows. Power consumption required for extension and contraction of the polymer actuators 40 is thus low. Consequently, a battery of low capacity may be used as the power supply 31.

(3) The principal portion of each polymer actuator 40 is formed into the cylindrical shape with openings at both ends by spirally winding the dielectric layer 41 and the electrodes 42 and 43. Making the polymer actuator 40 compact improves the mountability in the electric prosthetic hand.

Also, by the voltage application across the electrodes 42 and 43, the polymer actuator 40 can extend in the planar direction of the dielectric layer 41, that is, in the longitudinal direction of the polymer actuator 40. On the other hand, by stoppage of the voltage application, the polymer actuator 40 can also be contracted in the longitudinal direction of the polymer actuator 40.

(4) By simply screwing the bolt 53 as the first fastening member into the internal thread member 45 near the fixed end 48, the fixed side mounting portion 13 is sandwiched by the head portion 53B of the bolt 53 and the fixed end 48. That is, by a simple process of screwing the bolt 53, one of the two electrodes 42 and 43 is connected electrically to the fixed side mounting portion 13, and the fixed end 48 is also fastened to the fixed side mounting portion 13.

(5) The clamping portions 15 are provided at each bulging portion 14 of the fixed side mounting portion 13. Also, the bolt 53 is screwed in the state where the shaft portion 53A is inserted between the clamping portions 15. The shaft portion 53A, which is screwed into the internal, thread member 45, can thus be inserted between the clamping portions 15 from outside the fixed side mounting portion 13 and can be taken out to the outside of the fixed side mounting portion 13 from between the clamping portions 15. The polymer actuator 40 can thus be mounted and removed readily to and from the fixed side mounting portion 13.

(6) By simply screwing the bolt 54 as the second fastening member into the internal thread member 46 near the movable end 49, the movable side mounting portion 16 is sandwiched by the head portion 54B of the bolt 54 and the movable end 49. That is, by a simple process of screwing the bolt 54, the other of the two electrodes 42 and 43 is connected electrically to the movable side mounting portion 16, and the movable end 49 is also fastened to the movable side mounting portion 16.

(7) The pair of clamping portions 25 is provided at each bulging portion 24 of the movable side mounting portion 16. Also, the bolt 54 is screwed in the state where the shaft portion 54A is inserted between the clamping portions 25. The shaft portion 54A, which is screwed into the internal thread member 46, can thus be inserted between the clamping portions 25 from outside the movable side mounting portion 16 and can be taken out to the outside of the movable side mounting portion 16 from between the clamping portions 25. The polymer actuator 40 can thus be mounted and removed readily to and from the movable side mounting portion 16.

(8) The multiple polymer actuators 40 are used, and the polymer actuators 40 are arranged with the respective polymer actuators 40 being matched in extension and contraction direction. Also, the fixed ends 48 of the polymer actuators 40 are fastened by the bolts 53 to the common fixed side mounting portion 13. Also, the movable ends 49 of the polymer actuators 40 are fastened by the bolts 54 to the common movable side mounting portion 16. By this arrangement, even when the force output from each polymer actuator 40 is small, a large force is applied to the movable side mounting portion 16. The force by which an object to be held is held by both finger portions 33 and 37 can thus be increased.

(9) The polymer actuators 40 are arranged around the guide portion 17. The guide portion 17 guides the reciprocal motion of the movable side mounting portion 16. By this arrangement, the extension and contraction of the respective polymer actuators 40 can be transmitted to the movable side mounting portion 16 in a well-balanced manner.

(10) Each polymer actuator 40 is formed of the dielectric layer 41, which is made of the insulating polymer material, and the electrodes 42 and 43, which are made of the conductive polymer material. By this arrangement, even when a force that opens/closes the finger portions 33 and 37 is applied from the exterior, the force is absorbed by the extension and contraction actions of the polymer actuator 40.

The present invention may be modified as follows.

The fixed side mounting portion 13 may have, in place of the pair of clamping portions 15, a hole for insertion of the shaft portion 53A of the bolt 53, in each bulging portion 14. Similarly, the movable side mounting portion 16 may have, in place of the pair of clamping portions 25, a hole for insertion of the shaft portion 54A of the bolt 54 in each bulging portion 24. In this case, the polymer actuator 40, with which the bolts 53 and 54 are not mounted, is located between the fixed side mounting portion 13 and the movable site mounting portion 16. Thereafter, the bolts 53 and 54 are passed through the holes provided in the bulging portion 24 and screwed into the internal thread members 45 and 46.

The number of the finger portions 33 and 37 may be changed to no less than three.

As the polymer actuators 40, an ionic type may be adopted in place of the dielectric type. An ionic type polymer actuator is made up of a junction material of an ion-exchange resin and electrodes. This type of polymer actuator is formed by precipitating electrodes of gold, platinum, or the like, by electroless plating onto both surfaces of a fluorine-based ion-exchange resin film. With this polymer actuator, when a voltage of several, bolts is applied across the electrodes, positive ions move inside the ion-exchange resin and toward the negative electrode side. The difference in swelling thus arises between the top surface and the bottom surface of the polymer actuator, and the polymer actuator deforms elastically. On the other hand, when the voltage application is stopped, the polymer actuator returns to its original shape by its own elastic force. The polymer actuator thereby extends and contracts. The same advantages as those of the present embodiment are thus obtained, by applying the present invention to the ionic type polymer actuator.

A spring, a spring washer, or other urging members may be provided between the head portion 53B (54B) of the bolt 53 (54) and the fixed side mounting portion 13 (movable side mounting portion 16). The urging member urges the head portion 53B (54B) of the bolt 53 (54) and the fixed side mounting portion 13 (movable side mounting portion in directions away from each other. By this arrangement, even when there is a cap between the head portion 53B (54B) of the bolt 53 (54) and the fixed side mounting portion 13 (movable side mounting portion 16), the electrical connection and the fastening of the fixed end 48 (movable end 49) to the fixed side mounting portion 13 (movable side mounting portion 16) is achieved. This is because the urging member absorbs the gap.

By the same reason, an urging member may be arranged between the fixed side mounting portion 13 (movable side mounting portion 16) and the fixed end 46 (movable end 49) of the polymer actuator 40. This urging member also urges the fixed side mounting portion 13 (movable side mounting portion 16) and the fixed end 48 (movable end 49) of the polymer actuator 40 in directions away from each other. Further, the bolt 53 (54) and the internal thread member 45 may be integrated because the gap is absorbed by the urging member.

As long as the first fastening member (the second fastening member) electrically connects one (the other) of the two electrodes 42 and 43 of the polymer actuator 40 to the fixed side mounting portion 13 (the movable side mounting portion 16) and fastens the fixed end 48 (the movable end 49) to the fixed side mounting portion 13 (the movable side mounting portion 16), the first fastening member (the second fastening member) may, for example, be an assembled body of a rivet and a split pin. In this case, holes are opened respectively in the fixed end 48 (movable end 49) of the polymer actuator 40 and a shaft portion of the rivet. The split pin is passed through the holes of the polymer actuator 40 and the rivet and by bending a portion of the split pin exposed from both holes, the polymer actuator 40 can be fastened to the fixed side mounting portion 13 (movable side mounting portion 16).

The arrangement of the power transmitting portion 60 may be modified such that the first finger portion 33 and the second finger portion 37 are opened when the polymer actuators 40 extend, and the finger portions 33 and 37 are closed when the polymer actuators 40 contract.

In the above described embodiment, the mechanism that converts the forward/rearward motion of the movable side mounting portion 16 to rotational motion and transmits the converted motion to the first finger portion 33 and the mechanism that converts the forward/rearward motion of the movable side mounting portion 16 to rotational motion and transmits the converted motion to the second finger portion 37 are provided independently. These mechanisms may be united. Also, the structure of the power transmitting portion 60 may be modified.

The holding force of the prosthetic hand main body, which, is generated, by closing the first finger portion 33 and the second finger portion 37, may be changed as follows.

(i) The voltage applied to the electrodes 42 and 43 of each polymer actuator 40 may be changed. In this case, as the voltage increases, the holding force of the prosthetic hand main body increases.

(ii) The diameter of the polymer actuator 40 may be changed. In this case, as the diameter increases, the holding force of the prosthetic hand main body increases.

(iii) The number of the polymer actuators 40, which extend/contract, may be changed. In this case, as the number of the polymer actuators 40 increases, the holding force of the prosthetic hand main body increases. Specifically, the number of the polymer actuators 40 installed in the electric prosthetic hand may be changed or the number of the polymer actuators 40 to which a voltage is applied may be made changeable by control.

The present invention may be applied to a cellular phone that includes a vibration function.

The invention claimed is:

1. A mounting structure for mounting a plurality of polymer actuators onto an apparatus that includes the plurality of polymer actuators as a drive source, each polymer actuator is made of a polymer material and is formed into an elongated shape, each polymer actuator deforms elastically in accordance with voltage application and returns to its original shape in accordance with stoppage of the voltage application, thereby extending and contracting in an axial direction of the polymer actuator, and the apparatus operates using the extension and contraction of each polymer actuator, the mounting structure for each polymer actuator comprising:

a fixed side mounting portion, which is made of a conductive material, connected to a power supply, and arranged immovably;

a movable side mounting portion, which is made of a conductive material, connected to the power supply, arranged to be reciprocal, and transmits extension and contraction of the polymer actuator to the apparatus;

a fixed end, which is one of two ends of the polymer actuator;

a movable end, which is the other of the two ends of the polymer actuator;

a first fastening member, which electrically connects one of a pair of electrodes of the polymer actuator to the fixed side mounting portion and fastens the fixed end to the fixed side mounting portion; and a second fastening member, which electrically connects the other of the pair of electrodes of the polymer actuator to the movable side mounting portion and fastens the movable end to the movable side mounting portion, wherein the first and second fastening members are formed by a bolt, by fastening the first fastening member to the fixed end, the fixed side mounting portion is sandwiched by a head portion of the bolt and the fixed end, and by fastening the second fastening member to the movable end, the movable side mounting portion is sandwiched by a head portion of the bolt and the movable end, and wherein each polymer actuator is arranged such that the extension and contraction directions of each polymer actuator are matched, the fixed ends of each polymer actuator are fastened by the first fastening members to a common fixed side mounting portion, and the movable ends of each polymer actuator are fastened by the second fastening members to a common movable side mounting portion.

2. The mounting structure for a polymer actuator according to claim 1, wherein the polymer actuator includes a dielectric layer, which is made of an insulating polymer material having elasticity, and a pair of electrodes, which are made of a conductive polymer material having elasticity and sandwich the dielectric layer in the thickness direction of the dielectric layer, the polymer actuator causes the dielectric layer to extend in its planar direction in accordance with voltage application to the electrodes, and the polymer actuator causes the dielectric layer to contract and return to its original shape in accordance with stoppage of the voltage application.

3. The mounting structure for a polymer actuator according to claim 2, wherein the polymer actuator is formed into a cylindrical shape by spirally winding the dielectric layer and the electrodes.

4. The mounting structure for a polymer actuator according to claim 1, wherein the fixed side mounting portion includes a pair of clamping portions, and the bolt is screwed in a state where a shaft portion of the bolt is inserted between the clamping portions.

5. The mounting structure for a polymer actuator according to claim 1, wherein the movable side mounting portion includes a pair of clamping portions, and the bolt is screwed in a state where a shaft portion of the bolt is inserted between the clamping portions.

6. The mounting structure for a polymer actuator according to claim 1, further comprising:

a guide portion guiding a reciprocal motion of the movable side mounting portion, and the polymer actuators are arranged around the guide portion.

7. The mounting structure for a polymer actuator according to claim 1, further comprising:

a support column extending in the axial direction of the polymer actuator, wherein the fixed side mounting portion has a plurality of bulging portions, which bulge outward in radial directions of the support column.

8. The mounting structure for a polymer actuator according to claim 7, wherein each of the bulging portions includes a pair of clamping portions, which extends outward in radial directions of the support column.

9. The mounting structure for a polymer actuator according to claim 1, wherein the mounting structure is applied to an electric prosthetic hand.

* * * * *